United States Patent [19]

Conway

[11] 4,384,581
[45] May 24, 1983

[54] MICROSYRINGE

[75] Inventor: Hugh T. Conway, Cedar Grove, N.J.

[73] Assignee: Becton, Dickinson and Company, Paramus, N.J.

[21] Appl. No.: 293,784

[22] Filed: Aug. 18, 1981

Related U.S. Application Data

[62] Division of Ser. No. 112,961, Jan. 17, 1980, abandoned.

[51] Int. Cl.³ .............................................. A61M 5/00
[52] U.S. Cl. ................................................... 604/181
[58] Field of Search .......... 128/218 R, 218 P, 218 D, 128/218 A, 218 C, 215, 216, 234, 220, 221

[56] References Cited

U.S. PATENT DOCUMENTS

| 2,066,868 | 1/1937 | Whittaker | 128/234 X |
| 2,098,106 | 11/1937 | Pieck | 128/234 X |
| 2,771,217 | 11/1956 | Brown et al. | 128/218 C X |
| 3,216,616 | 11/1965 | Blankenship, Jr. | 128/218 C X |
| 3,604,417 | 9/1971 | Stolzenberg et al. | 128/218 A |
| 3,854,209 | 12/1974 | Franklin et al. | 128/234 X |
| 4,235,235 | 11/1980 | Bekkering | 128/218 R |

Primary Examiner—John D. Yasko
Attorney, Agent, or Firm—Richard J. Rodrick

[57] ABSTRACT

A microsyringe includes an elongated hollow tube having no piston, plunger or the like positioned in its lumen. A needle cannula is at one end of the tube in fluid communication with the lumen. A connector hub is at the other end of the tube for attachment to a device for providing a fluid movement force into the lumen.

6 Claims, 8 Drawing Figures

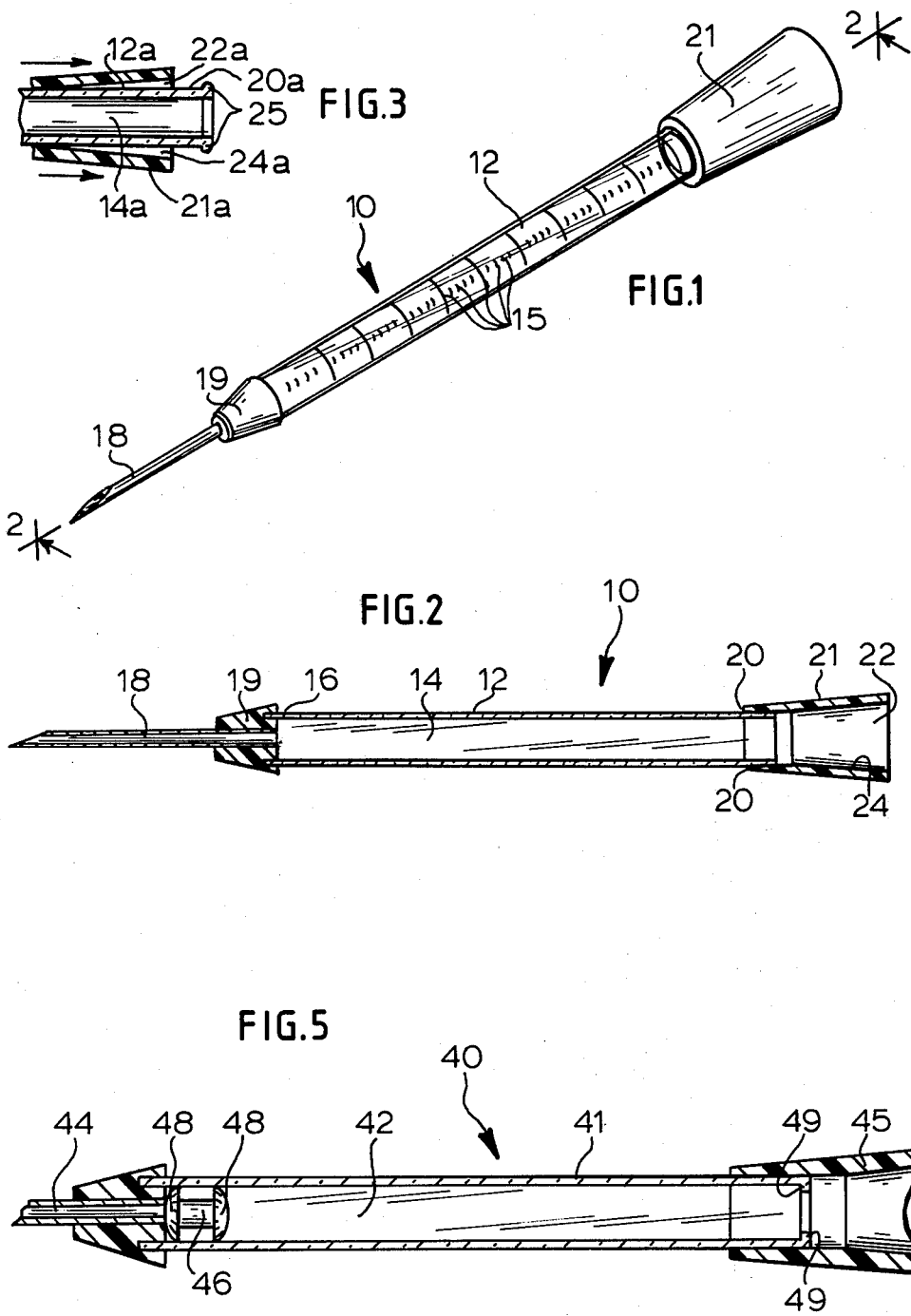

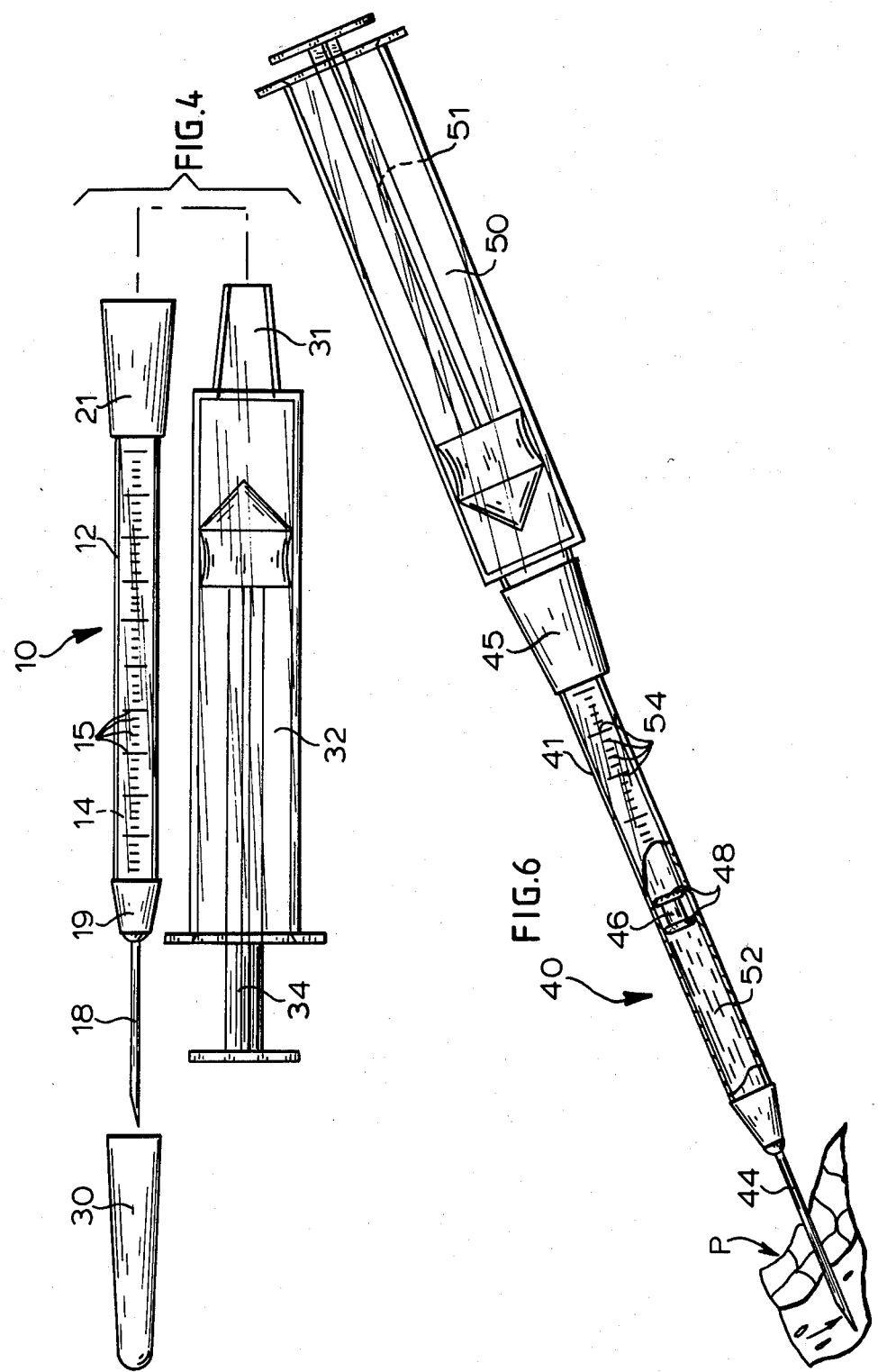

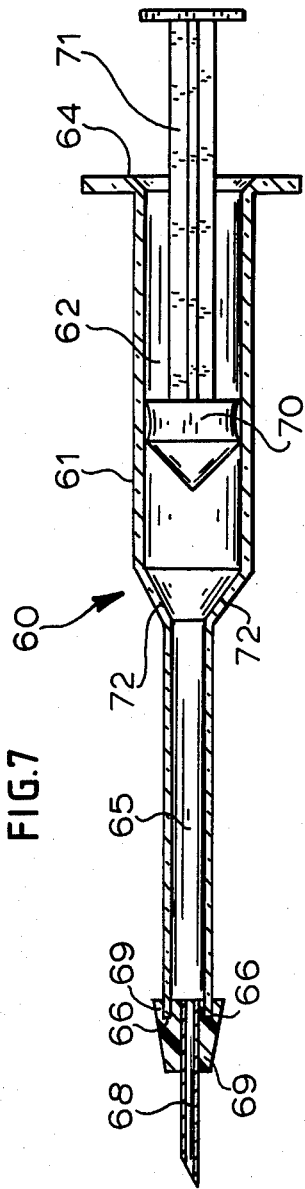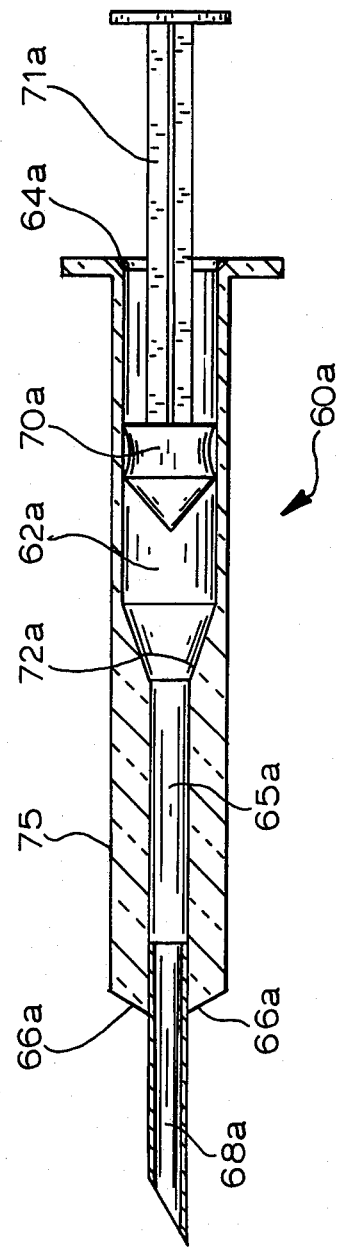

MICROSYRINGE

This is a division, of application Ser. No. 112,961, filed Jan. 17, 1980 now abandoned.

BACKGROUND OF THE INVENTION

The present invention relates to devices for the collection and injection of small volumes of fluid into an animal or human subject, or even inanimate objects, and more particularly, concerns a microsyringe useful for such purpose without the need for pistons, plungers or the like within the syringe.

There are many instances when small amounts of fluid have to be injected into or collected from a patient. For instance, some medications which are prescribed for a patient are in the microliter volume range. Use of standard hospital and medical type syringes for such a small volume range has proven impractical inasmuch as many of these syringes handle volumes in the milliliter volume range. However, microliter volume syringes have been fabricated and utilized for these small range applications. Generally speaking, these microliter volume syringes have been fabricated along the lines of the bigger syringes, i.e., they rely upon the incorporation of a slidable piston or plunger inside the barrel of the syringe. In such a small assembly, this piston must be matched inside the barrel with close accuracy in order for such a small syringe to be functional. This leads to a significantly high expense of manufacture. In addition, handling such a small syringe has been inconvenient, especially due to its fragility since most syringes of this small type are made of glass. The pistons in these syringes are also very thin and are easily damaged. Accordingly, with the deficiencies that are inherent, in the presently known and used small dose syringes, particularly in the microliter volume range, an improved microsyringe for small volume ranges is still being sought. Such an improvement to overcome the aforementioned deficiencies is the basis upon which the present invention is directed.

SUMMARY OF THE INVENTION

The microsyringe of the present invention comprises an elongated hollow tube having a completely free lumen. A needle cannula is at one end of the tube in fluid communication with the lumen. A connector hub is at the other end of the tube for attachment to means for providing a fluid movement force into the lumen.

In its preferred form, the elongated hollow tube is a slender capillary tube, cylindrically shaped and translucent. It may have graduations on its outside surface to indicate specific volume measurements of the microsyringe. No sliding piston or plunger is required in this microsyringe since it is intended to be used in tandem with a standard type syringe which provides the fluid driving force for suction and expulsion of the fluid within the microsyringe.

In another embodiment of the present invention, a microsyringe substantially as described above includes slidable indicator means in the lumen. The indicator means is in fluid-tight engagement with the inside surface of the tube and is slidably responsive to a fluid force entering the lumen. Especially when graduations are included on a translucent tube, the slidable indicator means provides an improved mechanism for the operator to determine the amount of fluid inside the tube.

In a further embodiment of the present invention, the slidable indicator means may be a flotation device instead of a fluid-tight movable indicator. For instance, the flotation device may be a small section of polyethylene or styrene foam which floats at the level of fluid in the microsyringe.

A further embodiment of the present invention includes a syringe which is useful in handling small doses of fluid. In this embodiment the barrel of the syringe includes a lumen extending therethrough. The lumen has two portions, a larger cross-sectional portion extending toward a proximal end of the barrel and a smaller cross-sectional portion extending toward a distal end of the barrel with the two portions of the lumen being in fluid communication with each other. The needle cannula extends from the end of the barrel in fluid communication with the smaller cross-sectional portion of the lumen. In this embodiment, a piston in the larger portion of the lumen serves as the fluid driving force to move fluid into or out of the smaller portion of this aspect of the syringe, with the smaller portion providing the capability of accurately handling and measuring small doses of fluid in or out of the syringe.

From the structural standpoint, the microsyringe of the present invention is notably different from prior syringes heretofor known. Particularly, in the preferred embodiment, there is no piston or plunger inside the hollow tube. A significant advantage of this construction is the ease of manufacture and low expense attendant therewith. Along these lines, the microsyringe can clearly be used as a disposable item. Also, the microsyringe may be used in tandem with a specific volume standard size syringe, or with any other mechanism to provide a driving force. Furthermore, measured volume can be controlled with considerably greater accuracy than that which the known small volume syringes provide. Further still, the connector hub of the microsyringe may be configured to mate with the tip of any convenient known syringe or other source of controlled pressure. In this way, the present microsyringe is assembled in tandem with an ordinary syringe in place of a standard needle assembly. Fluid pressures resulting from the motion of the piston of the ordinary syringe provide the fluid movement force within the microsyringe for either collection or injection of fluid into the subject. In the embodiment of the present invention which includes the slidable indicator, enhanced visibility of the fluid level is provided thereby making the measurement of fluid much easier. Furthermore, the indicator, which is prevented from sliding out of the hollow tube, serves as an effective stop to prevent any inadvertent overfilling which may tend to contaminate the ordinary driving syringe. These advantages, and others as well, will be more clearly perceived from a reading of the detailed description hereinafter taken in conjunction with the accompanying drawings.

BRIEF DESCRIPTION OF THE DRAWINGS

FIG. 1 is a perspective view illustrating one embodiment of the microsyringe of the present invention;

FIG. 2 is a cross-sectional view taken along line 2—2 of FIG. 1;

FIG. 3 is a partial cross-sectional view of the proximal end of the microsyringe illustrating the sliding nature of an alternative embodiment of the connector hub;

FIG. 4 is an exploded view of a microsyringe package of components for its utilization;

FIG. 5 is a cross-sectional view of an alternate embodiment of the microsyringe of the present invention;

FIG. 6 is a plan view illustrating the microsyringe of FIG. 5 in use with an ordinary standard syringe;

FIG. 7 is a cross-sectional view of another embodiment of the present invention with a unitary structure of syringe and microsyringe; and FIG. 8 is a cross-sectional view of an alternative embodiment of the invention illustrated in FIG. 7.

DETAILED DESCRIPTION

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be pointed out in the appended claims.

Adverting to the drawings, particularly FIGS. 1 and 2, there is illustrated a microsyringe 10 particularly useful for delivering to or collection from a patient small amounts of fluid. Microsyringe 10 is comprised of an elongated hollow tube 12 which is preferably a slender capillary tube. Tube 12 has a lumen 14 extending therethrough, with the lumen being empty and free of any elements such as a piston, plunger or the like. While tube 12 is illustrated as being cylindrically shaped with a circular cross-section, it may assume any convenient cross-sectional shape as may be desired. For example, the tube may have a triangular cross-section similar to that commonly used for fever thermometers in order to magnify the apparent image. In order to provide a clear observation of the level of fluid content inside the tube, it is preferably made of a translucent material, which may desirably be glass or plastic. If glass is used to fabricate the tube, its structure is substantially rigid; on the other hand, if plastic is used, the tube may be either substantially rigid or flexible, depending upon the choice of plastic materials. Various combinations of glass and plastic may be utilized in the construction of the tube. As a further aid to the operator in measuring the specific volume of fluid inside the tube, graduations 15 are included on the tube. Suitable inks, indentations, raised bosses or the like may be employed in providing these graduations. Concerning the overall size of capillary tube 12, it may vary according to the use for which it is intended. In most instances of use in the small volume range, it is expected that the capillary tube will hold a volume of fluid not exceeding one hundred (100) microliters. However, some applications may require larger total volumes such as five hundred (500) microliters.

At the distal end 16 of the capillary tube is a needle cannula 18 which is attached to the tube by means of an adapter 19. The needle cannula is thus in fluid communication with lumen 14. Metal, such as stainless steel or the like, or plastic material may be used to form the needle cannula, which may be straight or curvilinear, depending upon use of the microsyringe. This construction of the adapter on the distal end of the tube minimizes dead space in this end which is common in needle assemblies wherein the needle is spaced deeply within the adapter. Elimination of dead spaces in this construction keeps waste of any expensive fluids, which may be used, to a minimum. At the proximal end 20 of the capillary tube is a connector hub 21. As illustrated, particularly in FIG. 2, connector hub 21 preferably includes a receptacle portion 22 and a tapered surface 24 around the receptacle portion. This structure in most instances is preferably a tapered female Luer connection and is adapted to mate with a male Luer connection which is commonly found on the end of ordinary syringes or other sources of controlled pressure. It is noted that receptacle 22 which receives the male portion of the ordinary standard syringe is also in fluid communication with lumen 14 of the capillary tube. Thus, the movement of fluid through lumen 14 is controllable after the microsyringe has been attached to the controlled pressure source. Both needle cannula adapter 19 and hub 21 are preferably made of plastic material and may be assembled to the capillary tube using adhesive, such as epoxy, or mechanical interaction such as welding. It is appreciated that other materials may be used in fabricating the components of this invention, as well as other processes to assemble such components, as may be well known to those ordinarily skilled in the art.

Instead of fixedly attaching the connector hub to the capillary tube, the hub may be slip-fitted onto said tube as illustrated in FIG. 3. In this alternate embodiment, hub 21a is fitted around capillary tube 12a so that proximal end 20a can be exposed. With this feature, capillary tube 12a may be filled by capillary action with fluid entering the lumen 14a through the opening in proximal end 20a. A boss 25 or the like is provided at the proximal end of the capillary tube to prevent hub 21a from sliding off the surface of the tube. After this capillary tube is filled, hub 21a is available to receive the mating portion of an ordinary standard syringe or the like.

Turning now to FIG. 4, microsyringe 10 is illustrated in an exploded view with other components which contribute in making it more useful. For example, a shield 30 may be provided to protect needle cannula 18 by being slipped over the needle cannula and snugly fitting on adapter 19. It is appreciated that this shield may take on various forms depending upon many factors, and may either enclose just the needle cannula or may be a package in itself for enclosing the entire microsyringe. A sterility barrier may be included with shield 30 for sterilizing needle cannula 18 after the shield has been assembled. Shield 30 is to be removed before the microsyringe is used. Connector hub 21 is preferably adapted to mate with the male tip 31 of a standard syringe 32. It is appreciated that the configuration of the connector hub can be modified to adapt to various controlled pressure sources which the operator may be using. When using a standard syringe attached to connector hub 21, movement of its plunger 34 controls fluid movement through the lumen of capillary tube 12. In this regard, inward movement of plunger 34 will cause fluid to move toward the distal end of the capillary tube for delivery into a patient; outward movement of plunger 34 will cause fluid to move toward the proximal end of the capillary tube for withdrawing fluid from a patient. In either instance, the fluid levels inside capillary tube 12 are clearly observed by the operator with graduations 15 providing an accurate measurement of the volume of the fluid in the tube. After the microsyringe has been used, it may be detached from the ordinary syringe and either be discarded or else sent on to the laboratory for analysis of the collected fluid.

Referring now to FIG. 5, another embodiment of the microsyringe of the present invention is illustrated. In this embodiment, microsyringe 40 is substantially similar in most respects to the embodiments described above, and includes an elongated hollow tube 41 having a lumen 42 therethrough. A needle cannula 44 is at a distal end of the tube in fluid communication with lumen 42, and a connector hub 45 is at a proximal end of the tube for attachment to means for providing a fluid movement force into the lumen. In this embodiment, however, a slidable indicator 46 is included, and is preferably completely positioned within the lumen of the tube. Indicator 46, although slidable, is sized to provide a fluid-tight engagement with the inside surface of tube 41. To facilitate this engagement, protruding ribs 48 are preferably provided; the nature of ribs 48 provide an effective fluid-tight seal, but serve to minimize friction against the inside surface of the tube whereby sliding is facilitated. This indicator is preferably an elastomeric material such as rubber or plastic and may be made of a dark color to provide a good visual contrast through the translucent capillary tube for better visualization. Abutment stops 49, such as small nubs or the like, are located at the proximal end of the tube for preventing the slidable indicator from sliding out of the tube.

In another embodiment of this invention, the slidable indicator is a flotation element such as styrene foam. This flotation element is not in fluid-tight sealing engagement, as is the previously described elastomeric element. The flotation element slides by floating at the head of the fluid level inside the microsyringe.

In use, such as illustrated in FIG. 6, microsyringe 40 is matingly connected by way of its connector hub 45 to a standard syringe 50. In conjunction with movement of the standard syringe plunger 51, sliding indicator 46 is responsive to the force of a fluid 52 entering the lumen of the capillary tube. For example, as fluid is withdrawn from the patient P, slidable indicator 46 moves through tube 41 under the influence of the fluid force. Fill level of the fluid is easily determined by the operator by observing the dark slidable indicator through the translucent tube wall and noting the position against graduations 54. The abutment stops at the proximal end of the capillary tube prevent accidental overfill; in addition, since slidable indicator 46 also provides a fluid-tight seal, fluid which could cause contamination is prevented from entering into standard syringe 50.

Turning to FIG. 7, another embodiment of the present invention includes a syringe 60 useful in handling small doses of fluid. Syringe 60 is a one-piece, unitary structure which essentially combines the microsyringe portion with a standard syringe device. To this end, syringe 60 includes a barrel 61 which is preferably cylindrical shaped. Extending through barrel 61 is a lumen which is divided into two portions: a first portion of the lumen is a larger cross-sectional portion 62 which extends toward the proximal end 64 of barrel 61. This larger cross-sectional portion is open at the proximal end of the barrel. The other portion of the lumen is a smaller cross-sectional portion 65 which extends toward a distal end 66 of the barrel. This smaller cross-sectional portion is the microliter syringe portion and is generally fabricated to handle doses of fluid in the microliter range or extending up to about five hundred (500) microliters. At distal end 66 is a needle cannula 68 which is connected to that end by means of an adapter 69, along the same lines as a previously described embodiment. Needle cannula 68 is in fluid communication with smaller cross-sectional portion 65 of the lumen.

A slidable piston 70 is positioned in fluid-tight engagement with the inside walls of larger cross-sectional portion 62. A plunger arm 71, connected to piston 70, allows the operator to move piston 70 in or out depending upon the direction of the fluid movement. This piston serves as a fluid driving force for moving fluid into or out of the syringe. As can be seen by viewing FIG. 7, fluid is moved into or out of the smaller cross-sectional portion by movement of the piston either in the inward or outward direction. With appropriate graduations or other measuring techniques, particularly associated with the smaller portion, handling of very small doses of fluid can be managed accurately with this aspect of the invention.

It is noted in FIG. 7 that the wall thickness of the entire syringe is substantially constant and that the wall includes a tapered portion 72 which interconnects the smaller and larger cross-sectional portions of the lumen. With this construction, the outside diameter of the barrel is larger around the larger cross-sectional lumen than around the smaller cross-sectional lumen. Of course, other configurations are within the purview of the present invention. One such other configuration is illustrated in FIG. 8.

In the alternative embodiment in FIG. 8, the elements of the syringe are similar to the syringe illustrated in FIG. 7, with the letter designation "a" following elements of a nature corresponding to the syringe of FIG. 7. However, instead of a tapered portion in the wall of the syringe barrel, the barrel 75 of this embodiment has a substantially constant outside diameter. The taper 72a is still present in this embodiment in the lumen in the transition portion between larger cross-sectional portion 62a and smaller cross-sectional portion 65a. The embodiments illustrated in FIGS. 7 and 8 function essentially in the same fashion.

Although not shown, either embodiment of FIGS. 7 or 8 may include a suitable indicator element, particularly in the smaller cross-sectional portion, to indicate the level of fluid inside the smaller microliter portion. This indicator element would be substantially similar to that described in conjunction with FIGS. 5 and 6.

Thus, a microsyringe is provided for the collection or injection of fluid into a patient in the small volume range which eliminates the requirements of a mechanical piston, plunger or the like, and which is convenient to use, accurate in its measurement and disposable after use.

What is claimed is:

1. A microsyringe comprising an elongated, slender capillary tube having a lumen therethrough, a needle cannula at a distal end of said tube in fluid communication with said lumen, and a connector hub at a proximal end of said tube for attachment to means for providing a fluid movement force into said lumen, and a slidable indicator in said lumen, said indicator being slidable under the influence of a fluid force entering said lumen for indicating the amount of fluid inside said tube, said indicator being a flotation member which floats at the level of fluid in said lumen.

2. The microsyringe of claim 1 wherein said slidable indicator is positioned completely within said lumen, said microsyringe further comprising means for preventing said slidable indicator from sliding out of said lumen.

3. The microsyringe of claim 1 wherein said slidable indicator is made from an elastomeric material.

4. The microsyringe of claim 1 wherein said capillary tube is translucent and has graduations on its outside surface to indicate specific volume measurements.

5. The microsyringe of claim 1 wherein said capillary tube is rigid and is made of glass.

6. A microsyringe comprising an elongated hollow tube having a lumen therethrough, a needle cannula at one end of said tube in fluid communication with said lumen, a connector hub at the other end of said tube for attachment to means for providing a fluid movement force into said lumen, and slidable indicator means in said lumen, said indicator means being slidably responsive to a fluid force entering said lumen and being flotable at the level of fluid in said lumen.

* * * * *